United States Patent
Eriksson (10) Patent No.: US 8,303,561 B2
(45) Date of Patent: Nov. 6, 2012

(54) METHOD OF PRODUCING AN ABSORBENT GARMENT, AND AN ABSORBENT GARMENT PRODUCED ACCORDING TO THE METHOD

(75) Inventor: Katarina Eriksson, Lindome (SE)

(73) Assignee: SCA Hygiene Products AB, Gothenburg (SE)

( * ) Notice: Subject to any disclaimer, the term of this patent is extended or adjusted under 35 U.S.C. 154(b) by 183 days.

(21) Appl. No.: 12/739,555

(22) PCT Filed: Nov. 14, 2007

(86) PCT No.: PCT/SE2007/001008
§ 371 (c)(1),
(2), (4) Date: Apr. 23, 2010

(87) PCT Pub. No.: WO2009/064224
PCT Pub. Date: May 22, 2009

(65) Prior Publication Data
US 2010/0262109 A1    Oct. 14, 2010

(51) Int. Cl.
*A61F 13/15* (2006.01)
*B32B 37/00* (2006.01)
(52) U.S. Cl. ......... 604/385.22; 604/385.24; 604/385.25; 604/385.26; 604/385.27; 604/385.29; 156/264; 156/250; 156/256; 156/257
(58) Field of Classification Search ............. 604/385.22, 604/385.23, 385.24, 385.25, 385.26, 385.27, 604/385.29; 156/264, 250, 256, 257
See application file for complete search history.

(56) References Cited

U.S. PATENT DOCUMENTS

| | | |
|---|---|---|
| 4,692,368 A | 9/1987 | Taylor et al. |
| 4,842,596 A | 6/1989 | Kielpikowski et al. |
| 4,940,464 A * | 7/1990 | Van Gompel et al. ........ 604/396 |
| 5,143,679 A | 9/1992 | Weber et al. |
| 5,156,793 A | 10/1992 | Beull et al. |
| 5,167,897 A | 12/1992 | Weber et al. |
| 5,422,172 A | 6/1995 | Wu |

(Continued)

FOREIGN PATENT DOCUMENTS
EP    0 714 351    6/1996
(Continued)

OTHER PUBLICATIONS
International Search Report of PCT/SE2007/001008 dated Aug. 7, 2008.
(Continued)

*Primary Examiner* — Jacqueline F. Stephens
(74) *Attorney, Agent, or Firm* — Buchanan Ingersoll & Rooney PC (57) ABSTRACT

A method for continuously producing absorbent garments includes forming a continuous multi-component production web; and cutting individual garments from the production web. The production web is formed by: a) feeding a first elastic web in a travelling direction; b) stretching the first elastic web by 35-250% in the travelling direction; c) intermittently laying down absorbent cores in an intermediate zone extending in a travelling direction of the production web; d) feeding a continuous web of liquid permeable material in the travelling direction and covering the absorbent cores with the continuous web of liquid permeable material; and e) bonding the first elastic web to the continuous web of liquid permeable material in a first lateral zone on a side of the intermediate zone of the production web. In addition, an absorbent garment has a continuous liquid permeable layer.

32 Claims, 4 Drawing Sheets

U.S. PATENT DOCUMENTS

| | | | |
|---|---|---|---|
| 5,592,690 | A | 1/1997 | Wu |
| 5,634,216 | A | 6/1997 | Wu |
| 5,733,628 | A | 3/1998 | Pelkie |
| 5,861,074 | A | 1/1999 | Wu |
| 6,054,727 | A | 4/2000 | Voss |
| 6,149,637 | A | 11/2000 | Allen et al. |
| 6,313,372 | B1 | 11/2001 | Suzuki |
| 7,008,496 | B2 | 3/2006 | Morman |
| 2003/0105446 | A1 | 6/2003 | Hutson et al. |
| 2003/0226862 | A1* | 12/2003 | Vogt et al. ............... 223/37 |
| 2004/0112509 | A1 | 6/2004 | Morman |
| 2004/0127528 | A1 | 7/2004 | Eriksson et al. |
| 2004/0241389 | A1 | 12/2004 | Chung et al. |
| 2005/0101216 | A1 | 5/2005 | Middlesworth et al. |
| 2005/0103436 | A1 | 5/2005 | Otsubo et al. |
| 2005/0224171 | A1 | 10/2005 | Hoshika et al. |
| 2006/0083900 | A1 | 4/2006 | Ashraf |
| 2006/0108054 | A1 | 5/2006 | Ukegawa |
| 2006/0148358 | A1 | 7/2006 | Hall et al. |
| 2006/0148361 | A1 | 7/2006 | Ng et al. |
| 2006/0149208 | A1 | 7/2006 | Carr |

FOREIGN PATENT DOCUMENTS

| | | |
|---|---|---|
| EP | 0 715 351 A1 | 6/1996 |
| EP | 1 688 113 | 8/2006 |
| WO | WO 95/04654 | 2/1995 |
| WO | WO 95/18589 | 7/1995 |
| WO | WO 00/45764 | 8/2000 |
| WO | WO 02/02021 | 1/2002 |
| WO | WO 03/047488 A1 | 6/2003 |
| WO | WO 03/070140 A1 | 8/2003 |
| WO | WO 2004/078083 A1 | 9/2004 |
| WO | WO 2005/122985 | 12/2005 |
| WO | WO 2006/036090 A1 | 4/2006 |
| WO | WO 2006/073528 | 7/2006 |
| WO | WO 2006/093440 A1 | 9/2006 |
| WO | WO 2007/133127 A1 | 11/2007 |
| WO | WO 2008/060204 A1 | 5/2008 |
| WO | WO 2008/060205 A1 | 5/2008 |

OTHER PUBLICATIONS

Written Opinion of the International Searching Authority of PCT/SE2007/001008 dated Aug. 7, 2008.

International Preliminary Report on Patentability of PCT/SE2007/001008 dated Feb. 1, 2010.

E. Lakso, U.S. Appl. No. 12/739,594, entitle "Method for Producing an Absorbent Garment, and an Absorbent Garment Produced According to the Method" filed Apr. 23, 2010.

* cited by examiner

METHOD OF PRODUCING AN ABSORBENT GARMENT, AND AN ABSORBENT GARMENT PRODUCED ACCORDING TO THE METHOD

TECHNICAL FIELD

The invention relates to a method for continuously producing absorbent garments comprising forming a continuous multi-component production web and cutting individual garments from the production web. The invention also concerns an absorbent garment that can be produced according to the method.

BACKGROUND ART

Absorbent garments, particularly disposable pant-type absorbent garments include a pant-shaped chassis structure and an absorbent core component permanently integrated with the chassis. A major objective when designing pant garments is to make them resemble ordinary underwear as closely as possible. For this reason, the garment chassis usually comprises a material that is elastically stretchable, at least in the areas intended to be applied over the wearer's hips. In addition, absorbent garments such as pant diapers, sanitary pants and incontinence pants are designed to fit comfortably and snugly about the wearer and it is desired that they have a minimum of seams and joins that could cause discomfort such as chafing.

Further, absorbent pant-type garments should be capable of being pulled up and down over the hips of the wearer in the manner of a pair of underpants to allow the wearer or caregiver to easily remove a soiled garment and to replace it with a new clean garment. A particular problem with pant-type garments is that seams and joins running in a direction parallel to the waist edge of the garment may rupture when the user or a care-giver is pulling on the garment. In order to avoid this problem, it has to be ascertained that joins between different parts of the disposable pant-type garment are sufficiently strong to withstand the forces arising during normal use. However, strong seals and joins are commonly obtained by increasing the bonding area and/or by using more binder materials or severe binding conditions, resulting in stiffer and more uncomfortable joins.

A further requirement of particular importance for disposable garments is that the garment can be produced by an economically efficient process, involving as few process steps and components as possible.

Hence, there exists a continuing need for an improved process of making a pant-type absorbent garment having a chassis including one or more elastically stretchable components.

Accordingly, an object of the invention is to provide a simple and economic method for producing an absorbent garment such as an elastically stretchable pant-type garment.

DISCLOSURE OF INVENTION

In accordance with the invention, there is provided a method for continuously producing absorbent garments comprising forming a continuous multi-component production web and cutting individual garments from the production web, the method for forming the production web comprising the steps of a) feeding a continuous web of liquid permeable material in a travelling direction, the web of liquid permeable material having an intermediate zone extending in the travelling direction and a first and a second lateral zone on each side of the intermediate zone, b) intermittently laying down absorbent core components in the intermediate zone of the first web of liquid permeable material;

c) feeding a first elastic web in the travelling direction;

d) stretching the first elastic web by 35-250% in the travelling direction, e) laminating the first elastic web to the continuous web of liquid permeable material in the first lateral zone of the continuous web of liquid permeable material.

The method according to the invention offers a highly economical and efficient way of producing disposable absorbent garments. The finished garments in accordance with the invention have a tailored appearance with a soft continuous inner body-contacting layer and an outer surface that may be a nonwoven or elastic film layer, as desired. The method makes it possible to use a minimum of material layers and components that have to be joined to each other thus reducing production times as well as production costs.

An absorbent garment as used herein refers to all kinds of absorbent hygienic garments that are worn as a pair of underpants and that have a waist opening and two leg openings. Garments according to the invention include pant-diapers and open-type diapers for all kinds of users as well as absorbent hygienic panties for feminine protection and incontinence.

In this context, an elastic material is defined as a material having a permanent elongation after relaxation of less than 10% after the material has been subjected to an elongation of 30% in the elasticity test specified hereinafter.

A non-elastic material is a material that does not fall within the definition of an elastic material. Accordingly, a non-elastic material as used herein is a material that may be stretchable or non-stretchable. In the case of a stretchable material, the material has a permanent elongation after stretching and relaxation of more than 10% after having been subjected to an elongation of 30% as determined according to the elasticity test.

The elastic web may be adhesively bonded to the continuous web of liquid permeable material or may be thermally or ultrasonically bonded to the continuous web of liquid permeable material.

Thermal or ultrasonical bonding can be in the form of individual bond elements such as spot bonds or line bonds or can be in the form of a continuous bond pattern. By selecting a bond pattern of sparsely distributed spot bonds, it is possible to achieve a higher flexibility in the resulting laminate than with a pattern of bonds occupying a large proportion of the interface between the bonded layers.

The method according to the invention may further include the steps of:

f) feeding a second elastic web in the travelling direction;

g) stretching the second elastic web by 35-250% in the travelling direction; and h) laminating the second elastic web to the continuous web of liquid permeable material in the second lateral zone of the continuous web of liquid permeable material.

The first and second elastic webs may be bonded to the continuous web of liquid permeable material with a gap located between the first and second elastic webs in the intermediate zone of the continuous web of liquid permeable material.

The elastic web or webs may be elastic film, elastic nonwoven or an elastic laminate comprising at least one elastic film and/or elastic nonwoven material. The elastic webs may form elastic waist panels and elastic front and back panels in the finished pant-type absorbent garment. In one embodiment of the invention, the elastic web is a laminate of an elastic film and a nonwoven layer and the elastic web is bonded to the continuous web of liquid permeable material with the elastic film facing the continuous web of liquid permeable material.

An elastic material that has previously been used to form elastic panels in absorbent garments such as pant-type diapers is a laminate comprising an elastic film sandwiched between two layers of non-elastic nonwoven. In order to render the laminate elastically stretchable, it is subjected to an activation treatment. A three-layer, activated laminate is disclosed in International Patent Application No. WO 03/047488. The activated laminate is produced by incrementally stretching an elastic film layer between two non-elastic cloth-like layers. Incremental stretching is carried out by passing the laminate between intermeshing gear rollers. Activation of elastic laminates by incremental stretching is also disclosed in U.S. Pat. Nos. 5,143,679, 5,156,793 5,167,897, 5,422,172, 5,592,690, 5,634,216 and 5,861,074. The non-elastic cloth-like layers are fully or partially broken or torn during the activation process so that the elasticity of the laminate after activation is determined mainly by the elasticity of the elastic film layer. In the three-layer laminate in WO 03/047488, the non-elastic layers are completely broken so that the elasticity of the activated laminate is substantially the same as the elasticity of the elastic film layer.

The disclosed laminates have excellent comfort properties and are soft, breathable and elastic. Unfortunately, the activation process reduces the tensile strength and puncture resistance of the material so that when used as a chassis component in a disposable pant garment, the material is easily torn when exposed to the forces arising when putting on or taking off the pant garment. In order to increase the tensional strength of an activated laminate and to overcome the tearing problem, it has been proposed in PCT/SE2006/000563 to bond a stretch-activated two-layer laminate comprising a nonwoven layer and an elastic film layer to a second nonwoven layer while the two-layer laminate is in a stretched state.

For the purpose of the invention, it is also possible to use stretch-bonded elastic laminates comprising an elastic film or nonwoven web that has been bonded to at least one non-elastic layer with the elastic layer being stretched in at least one direction during the bonding step.

Another type of elastic laminates that could be used in the method according to the invention is "neck bonded" laminates, which are laminates in which an elastic material is bonded to a non-elastic material while the non-elastic material is extended under conditions reducing its width. A neck bonded laminate is a composite material having at least two layers in which one layer is a necked, non-elastic layer and the other layer is an elastic layer.

The elastic film used for producing the elastic laminates may be of any suitable elastic polymer, natural or synthetic. One example of an elastic film that has proven to provide good elasticity and breathability is an apertured three-layer elastomeric film with the composition polyethylene-styrene/ethylene/butadiene/styrene-polyethylene (PE-SEBS-PE).

The elastic web or webs used in the process in accordance with the invention may be composed of a layer of fibrous material and an elastic layer. The fibrous layer is preferably chosen so that it provides a soft and cloth-like feel and appearance to the laminate. Examples of suitable materials are meltblown webs, spunbond materials, and creped nonwovens. Creped nonwovens generally have greater extensibility and flexibility than non-creped nonwovens. By using a creped nonwoven, the laminate will be more conformable and extensible than is possible with a non-creped nonwoven.

The basis weight of the nonwoven web used in the elastic laminate is suitably from 10-80 $g/m^2$ and preferably from 10-30 $g/m^2$. Examples of suitable polymers used in the fibrous material are polyesters, polyethylene, polypropylene and other polyolefin homopolymers and copolymers. Natural fibres, for example cotton, may also be used as long as they provide the desired properties. A mixture of polymers can contribute to a higher flexibility of the nonwoven layer and give the nonwoven material a higher elongation at maximum load. A mixture of polyethylene and polypropylene polymers has proven to provide good results in this respect. However, nonwovens having different fibre mixtures may also be used.

The elastic layer is preferably an apertured elastic film. The elastic layer may have a basis weight of between 10 and 120 $g/m^2$, preferably between 15 and 60 $g/m^2$. The elastic layer may be of any suitable elastic polymer, natural or synthetic. Some examples of useful materials for the elastic layer are low crystallinity polyethylenes, metallocene-catalyzed low crystallinity polyethylenes, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable elastic film is an apertured three-layer elastomeric film with the composition polyethylene-styrene/ethylene/butadiene/styrene-polyethylene (PE-SEBS-PE).

In accordance with the invention, the continuous web of liquid permeable material constitutes a reinforcement layer for the elastic web. Hence, it is possible to use an elastic two-layer laminate or an elastic film layer to elasticise the absorbent garment instead of the prior art three-layer laminates. An elastic two-layer laminate may be manufactured and activated according to either of the methods disclosed in WO 03/047488 or EP 0 715 351 by applying the nonwoven web to one side of the film. The nonwoven web and the film may be extrusion bonded or may be bonded by adhesive. The laminate is incrementally stretched to activate the elasticity of the film layer. Incremental stretching can be made to a point below the elongation at peak load of the nonwoven web to retain some strength in the nonwoven web. Alternatively, the stretching may be carried out so that the nonwoven is completely torn, as disclosed in WO 03/047488.

When laminating a two-layer stretch-activated laminate to the continuous web of liquid permeable material, the two-layer laminate is preferably bonded to the continuous web of liquid permeable material with the film side of the laminate facing the continuous web of liquid permeable material. Thereby, a three-layer laminate is created having a smooth face on the surface where the two-layer laminate is arranged and a somewhat gathered, puckered face on the opposing surface, where the continuous web of liquid permeable material is arranged. In this manner, an absorbent garment having a smooth surface in contact with any clothing worn over the absorbent garment is obtained. The smooth surface of the laminate is aesthetically pleasing and will be less conspicuous when the absorbent article is worn under thin or tight-fitting garments.

Before laminating the elastic web to the continuous web of liquid permeable material, the elastic web is stretched, preferably in the travelling direction, or machine direction, MD by 35-250% of its initial, non-stretched extension and is held in the stretched state during the lamination step. By choosing and controlling the amount of stretch, it is possible to obtain a selected elasticity in the end product. The elastic web is preferably stretched by 35-180% of its non-stretched extension, more preferably by 50-150% of its non-stretched extension, and most preferably by 70-120% of its non-stretched extension during lamination with the continuous web of liquid permeable material.

The amount of stretching of the elastic web is specified as a percentage of the initial, non-stretched extension of the laminate in the direction of stretch. Accordingly, a laminate having a first, non-stretched length of 1 m and being stretched by 50% has a second, stretched length of 1.5 m.

The elastic web can be adhesively bonded to the continuous web of liquid permeable material. Alternatively, the elastic web can be thermally or ultrasonically bonded to the continuous web of liquid permeable material. Thermal or ultrasonical bonding can be in the form of discreet bonds such as spot bonds or line bonds. By selecting a bond pattern of sparsely distributed spot bonds, it is possible to obtain a material having higher flexibility and conformability than with a bond pattern occupying a large proportion of the interface between the bonded layers.

A major advantage of the method according to the invention is that it is possible to use a single layer of elastic material such as an elastic film or a two-layer film/nonwoven laminate and still obtain a sufficiently strong elastic panel in the finished absorbent garment. When a two-layer film/nonwoven laminate is used and placed with the nonwoven layer on the outside of the absorbent garment, the overall appearance of the garment will be that of a textile panty with soft and comfortable inner and outer surfaces. The elimination of a layer of material in the garment constitutes a considerable material saving and a corresponding cost saving.

The method according to the invention preferably comprises applying a liquid impermeable material on one surface of each absorbent core.

The cores may be at least partially covered with a liquid impermeable material on a surface of each core facing away from the continuous web of liquid permeable material when the absorbent core has been joined to the production web. The liquid impermeable material may be applied to the cores before joining the cores with the continuous web of liquid permeable material or after the cores have been joined with the continuous web of liquid permeable material.

The absorbent core may be bonded to a web of liquid impermeable material, the liquid impermeable web then being cut between the cores into core components comprising an absorbent core and a liquid impermeable barrier layer. Alternatively, the cores are bonded to the web of liquid impermeable material which is subsequently introduced into the production web, without cutting individual core components from the web.

The core components are then transferred to the continuous web of liquid permeable material and laid down on the continuous web of liquid permeable material with the liquid impermeable barrier layer facing away from the continuous web of liquid permeable material. Depending on how the cores are oriented during bonding to the web of liquid impermeable material, the core components may have to be turned and/or rotated so that the cores are facing the continuous web of liquid permeable material and are applied with the longitudinal direction of the cores aligned with the cross-machine direction of the continuous web of liquid permeable material.

Alternatively, the liquid impermeable material may be applied over the absorbent cores after the cores have been laid down on the continuous web of liquid permeable material.

The liquid impermeable barrier layer should have a width that is smaller than the width of the continuous web of liquid permeable material. Accordingly, the liquid impermeable barrier layer should not extend all the way to the edges of the production web and should preferably have the same or only slightly greater extension in the cross-machine direction, CD, of the production web than the cores. The CD extension of the liquid impermeable barrier layer may preferably not be more than 4 cm greater than the CD extension of the cores.

The core components may include further elements such as a supplementary topsheet material which may be a fluid acquisition material, liquid transport members, elastic members, shape-stabilizing members, shaping elements or the like. The components included in the core component can be connected to one another in a conventional manner, for example by adhesive bonding, ultrasonic welding or thermowelding.

The method according to the invention may further include attaching one or more leg elastic members to the production web. The leg elastic members may be applied to the continuous web of liquid permeable material before laying down the cores. Alternatively, the leg elastic members are applied to the production web after the cores have been laid down. A further option is to apply the leg elastic members to a separate carrier material that is then incorporated into the production web. When the leg elastic is applied in a pattern extending across the cores, it may be advantageous to deactivate parts of the elastic member or members extending over the cores. Deactivation may be accomplished in any known manner such as by treating the elastic members with chemicals or heat or by simply cutting the elastic members.

Leg elastic may be applied in any known manner and using any known and commonly used elastic materials. One example of a suitable method of arranging leg elastics is disclosed in WO 2004/078083.

The method according to the invention preferably also includes arranging an elastic waist band along at least one of the edges of the production web. A waist band can be formed by attaching discrete or continuous elastic elements along at least one edge of the continuous web of liquid permeable material and optionally covering the elastic elements with a nonwoven web which may be a folded-over portion of the continuous web of liquid permeable material or a separate nonwoven strip.

An elastic waist band can alternatively be joined to the production web as a separate component that has been prefabricated or that is manufactured in line with the production web.

The elastic waist band is preferably continuously joined to or arranged on the production web and may comprise an elastic band of any suitable kind of material such as elastic laminates, elastic foam strips, elastic nonwovens, non-elastic materials that have been elasticised with elastic threads or strings, etc. A commonly used elastic waist band is made by attaching elastic elements such as threads, bands or strings in a pre-tensioned state between two layers of nonwoven, non-elastic material. All commonly used elastic materials including natural or synthetic rubber, elastic foam, etc. can be employed. A waist band of this type may include two separate layers of nonwoven or may comprise a single layer of nonwoven material that is folded into a two-layer structure. Preferably, the elastic waist band includes a portion of the continuous web of liquid permeable material. An advantage of using the continuous web of liquid permeable material when forming the waist band is that the number of stiff and uncomfortable seams and joins can be reduced, giving the garment a soft and tailored appearance and feel. It is particularly preferred to arrange the waist band so that the inner surface of the hygienic garment is smooth without any potentially chafing irregularities.

The elastic waist band may include one or more components of the production web such as the first continuous web of liquid permeable material. In these embodiments, the elastic waist band may include an edge portion of an elastic or non-elastic part of the production web. In a particularly preferred embodiment, the elastic waist band is formed by attaching elastic elements to an edge portion of the first continuous web of liquid permeable material web and subsequently folding the continuous web of liquid permeable material to cover the elastic elements. It is also possible to attach elastic elements to an edge portion of the production web and leave the elastic elements non-covered, or covered by a separate web. If the elastic waist band incorporates an elastic web arranged at an edge portion of the first continuous web of liquid permeable material, the elastic web may be folded to create an edge portion having higher elastic retraction force than the non-folded portion of the part of the production web including only a single elastic web. The folded elastic web may be supplemented by additional elastic elements, if desired.

The method according to the invention may further include any conventional pant-forming production steps such as one or more of the following:
   a) applying leg elastic;
   b) applying raised barriers;
   c) cutting the production web to form leg openings;
   d) folding the production web;
   e) applying fastening elements to the production web;
   f) forming side joins in the folded web, and
   g) separating individual pant-type absorbent garments from the production web by cutting at the side joins.

Raised barriers are commonly used in diapers and similar absorbent garments and. The barriers are attached to the inner surface of the absorbent garment and are often made of hydrophobic nonwoven material. The raised barriers are often elasticated in order to hold the barriers in the raised position.

As an alternative to the formation of side joins, the method may include attaching fastening elements to the production web or to the separated individual absorbent garments.

The invention also offers an absorbent garment comprising a chassis structure comprising a front panel having a front end edge and first and second side edges, a back panel having a back end edge and first and second side edges and a crotch panel being arranged between the front and back panels and elasticated front and back waist panels being arranged along the front and back end edges of the front and back panels, and a core component being integrated with the chassis structure and forming an integral part of the absorbent garment, the chassis structure including a liquid permeable material having a garment facing side and a user facing side and forming a liquid permeable surface layer in the garment. The liquid-permeable material extends continuously between the front end edge and the back end edge and at least one of the front panel and the back panel comprises an elastic web that has been bonded to the liquid permeable material with the elastic web stretched by 35-250% in at least one direction.

The elastic web in the front and back panels preferably extends from the waist edges all the way to the leg openings of the garment.

According to an embodiment of the invention, the liquid permeable material forms part of one or both of the elasticated front and back waist panels.

An elastic web may have been bonded to each of the front panel and the back panel, the garment having a gap between the elastic webs in the crotch panel.

The absorbent garment may be a pant-type garment having the first and second side edges of the front panel being joined by edge joins to the corresponding first and second side edges of the back panel.

The elastic waist panels of the absorbent garment according to the invention may comprise elastic elements that are attached to the liquid-permeable material either on the outer garment-facing side of the liquid-permeable material or on the inner, user-facing side of the liquid-permeable material. The liquid-permeable material may be folded over to cover the elastic elements and may be secured in the folded over configuration by adhesive, thermobonding or ultrasonic welding. The elastic waist panels may comprise a portion of the at least one elastic web.

In accordance with the invention, the absorbent garment has a reinforcing member which is the continuous inner liquid-permeable surface layer or topsheet. The continuous inner surface layer is preferably a non-elastic material and preferably comprises a layer of nonwoven material. Useful materials include meltspun, meltblown and carded nonwovens. The materials may be thermobonded, hydroentangled, needled, thru-air bonded, or bonded with a bonding agent, as desired. The use of a continuous inner layer in the garment reduces the risk of breaking seams and joins between other components in the garment and of tearing materials that have low tensile strength such as stretch-activated elastic segments when putting on the garment. Moreover, seams and joins between components that are bridged by the continuous material can be made less strong, thus reducing welding times in the production process. Further, when less severe bonding conditions and less overlap between materials have to be used, the seams and joins can be made softer and less stiff than in conventional absorbent garments, implying that conformability and comfort of the garment is improved without risking that the garment will break or fall apart during production and handling.

The smooth and continuous inner surface is also beneficial in that it enhances wearer comfort and reduces the risk of chafing and skin irritation.

The garment may be a pant-type garment having the first and second side edges of the front panel joined by edge joins to the corresponding first and second side edges of the back panel. Alternatively, the garment may be of the open type which is provided with fastening elements that are used to fasten together the front and back panels of the garment when it is being put on a user.

The elastic waist panels may comprise elastic elements that are attached to the liquid-permeable material. The elastic elements may be attached to the garment-facing side of the liquid-permeable material or to the user-facing side of the liquid-permeable material. The liquid-permeable material may be folded over to cover the elastic elements or the elastic elements may be uncovered or covered by a separate material.

Further, the elastic waist panels may comprise a portion of the at least one elastic web.

BRIEF DESCRIPTION OF THE DRAWINGS

The invention will in the following be described in greater detail with reference to the appended drawings, wherein.

DETAILED DESCRIPTION OF THE INVENTION

Figure 1:
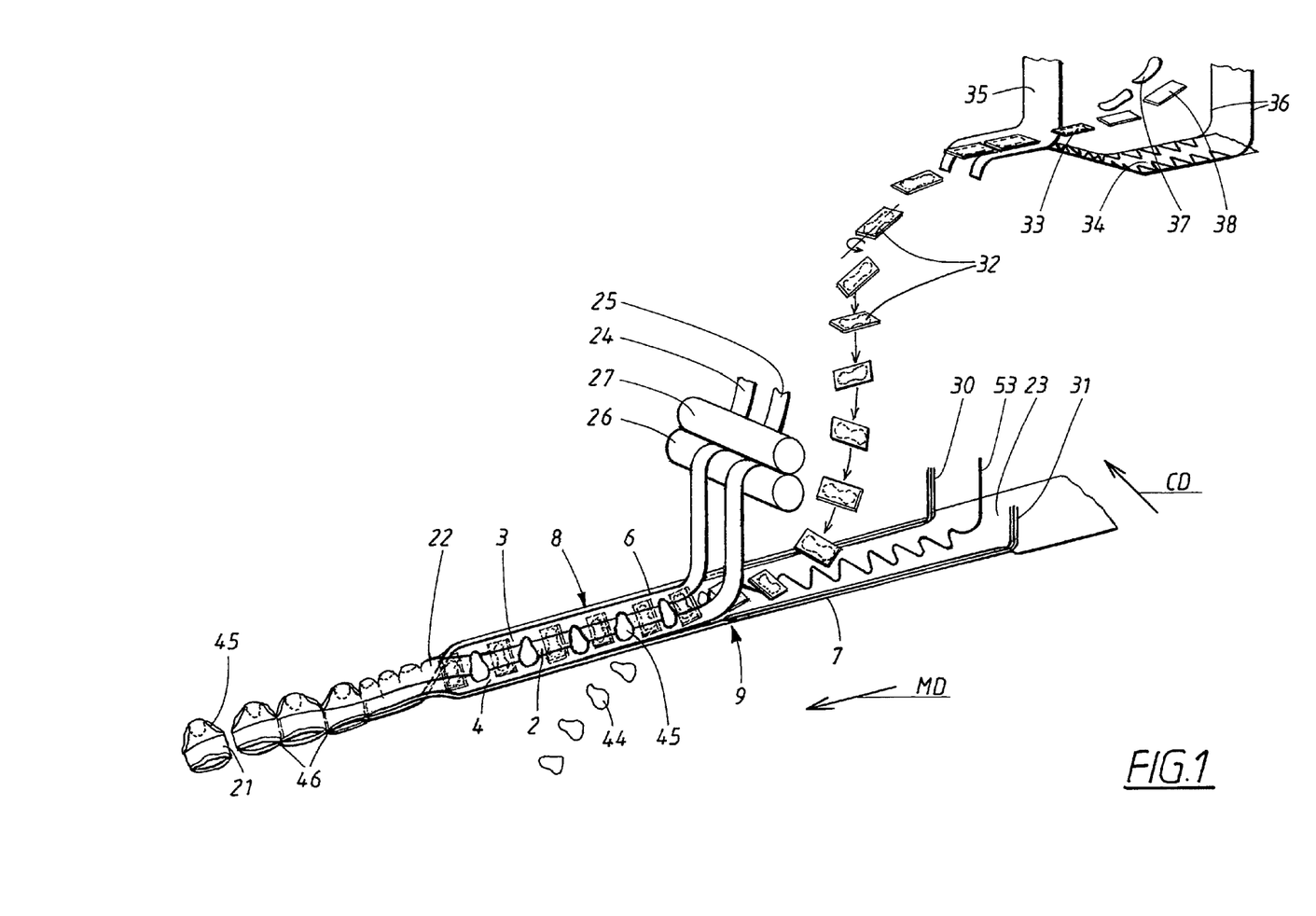
FIG. 1 shows schematically a method for producing pant-type absorbent garments in accordance with the invention.

FIG. 1 shows schematically a method for continuously producing absorbent garments, in particular pant-type diapers, although open-type diapers may be formed by basically the same method. The method involves forming a continuous multi-component production web and cutting individual diapers from the production web.

In FIG. 1, a diaper chassis structure is formed from a compound production web 22, comprising a continuous base web 23 of liquid-permeable material and first and second elastic webs 24,25 and first and second waist elastic elements 30,31. The elastic webs 24,25 may be elastic films, elastic nonwoven webs or elastic laminates, as previously disclosed.

The continuous base web 23 is fed in a travelling direction, the machine direction MD. The continuous base web 23 has an intermediate zone 2 extending in the machine direction MD and first and second lateral zones 3,4 on each side of the intermediate zone 2. Each lateral zone 3, 4 includes an edge zone 6,7 which is the part of the lateral zone 3,4 closest to the side edges 8,9 of the continuous base web 23. The continuous base web 23 is shown to have the different zones 2,3,4 symmetrically distributed in the cross machine direction CD with the intermediate zone 2 centrally located between the lateral zones 3,4 and the lateral zones 3,4 having equal widths. However, for other embodiments of the invention, the intermediate zone may be offset towards one of the side edges 8,9 of the continuous base web 23 implying that the lateral zones 3,4 have different widths.

Core components 32 are produced in a separate process and are intermittently laid down on the continuous base web 23. The core components 32 are placed in the intermediate zone 2 of the continuous base web 23 with portions of the core component s 32 extending into each lateral zone 3,4. If desired, the core components 32 may be bonded to the continuous base web 23 with adhesive or by any other conventionally employed bonding method.

Figure 2:
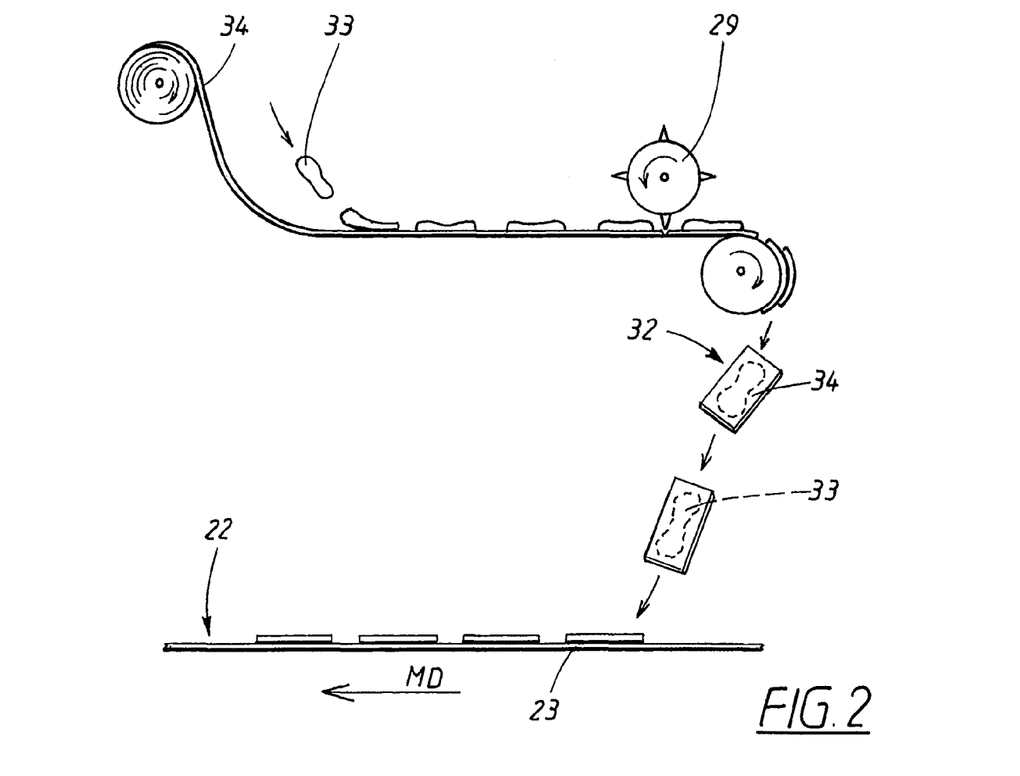
FIG. 2 shows the production of a core component for use in the method according to the invention.

The core components 32 may be produced as shown in FIG. 2, the process including feeding a web of liquid impermeable material 34 and laying down and bonding absorbent cores 33 to the web of liquid impermeable material 34. Individual core components 32 are formed by severing the web of liquid impermeable material 34 between the absorbent cores 33 at a cutting station 29. The cutting station 29 is shown as a cutting wheel, but may be any kind of cutting apparatus. It is also conceivable to cut the liquid impermeable web into a shape corresponding to the shape of the absorbent core 33 or into any other suitable shape.

Before laying down the core components 32 on the continuous web of liquid permeable material 23, the core components 32 are turned so that the liquid impermeable barrier material is facing towards the continuous web of liquid permeable material 23. Moreover, the core components 32 are rotated to bring the longitudinal direction of the cores 33 in alignment with the cross machine direction, CD of the continuous web of liquid permeable material 23.

The core components in FIG. 2 may, of course, comprise additional elements as conventional in the art.

FIG. 1 shows the production of a more complex core component 32 that comprises an absorbent core 33 arranged between a liquid barrier layer 34 and a liquid pervious layer 35. In the shown example, the core component 32 further comprises elastic elements 36 arranged in curve-shaped patterns on the liquid barrier layer 34. The shown pattern is only intended as an example and other patterns may be used for the elastic elements 36 such as linear elastic elements. It is also possible to dispense with elastic elements in the core component 32 altogether. The absorbent core 33 is shown as a two-layer structure with an upper, smaller absorbent layer 37 and a lower somewhat larger layer 38. It is to be understood that the construction of the core component 32 and the absorbent core is by no means limiting for the invention. Hence, any commonly employed core concepts and materials may be used in the process according to the invention. In addition, the core may have any suitable shape and size, as required by the intended use that the garment is designed for.

The core components 32 are laid down on the continuous base web 23 with the liquid pervious layer 35 facing the continuous base web 23. In this manner, the continuous base web 23 will form a liquid permeable topsheet on the finished absorbent garment and the liquid pervious layer 35 of the core component 32 will form a supplementary topsheet layer such as a liquid acquisition layer beneath the topsheet. In an alternative embodiment, the core components 32 may be made without the liquid pervious layer 35, the continuous base web 23 then forming a single topsheet layer on the finished absorbent garment.

As an alternative to forming core components including a barrier layer, the barrier layer may be applied over the absorbent cores after the cores have been laid down on the continuous liquid permeable base web 23.

After joining of the core component 32 with the continuous base web 23, first and second elastic webs 24,25 are laminated to the continuous base web 23 in the lateral zones 3,4. Lamination may be carried out by means of any suitable lamination process such as by using a binder, by thermo-bonding, ultrasonic welding, etc.

Before joining the elastic webs 24,25 to the web of liquid-permeable material 23, the elastic webs 24,25 are stretched at least in the machine direction (MD) by 35-250% of their initial, non-stretched extension. As shown in FIG. 1, stretching may be carried out by passing the webs between a pair of rollers 26,27 driven at different speeds. By controlling the amount of stretch, a predetermined elasticity can be obtained in the finished diaper chassis. The elastic webs 24,25 are preferably stretched by 35-180% of their non-stretched extension, more preferably by 50-150% of their non-stretched extension and most preferably by 70-120% of their non-stretched extension. The elastic webs 24,25 need not be stretched to the same extent if different elasticity is desired in different portions of the chassis structure. It is also possible to use different types of elastic materials in the elastic webs 24,25.

The degree of stretching of the elastic webs 24,25 during the formation of the production web 22 is a major means of achieving a selected elasticity in the portions of the production web 22 where the elastic webs 24,25 are attached.

It is preferred to use a nonwoven material having thermoplastic properties for the continuous base web 23 because a web containing thermoplastic material can be joined to other components by thermo-welding and ultrasonic welding techniques. The nonwoven layer can also be used to form side joins with good tensile strength. The side joins are preferably breakable side joins, i.e. welds that may be peeled or torn apart when the garment is removed after use.

Waist elastic elements 30,31 are attached along the edges 8,9 of the continuous base web 23 in the edge zones 6,7 and the elastic elements are then covered by folding the continuous base web 23 over the elastic elements 30,31 to form a waist band along each edge of the production web 22. In the process in FIG. 1, the elastic elements 30,31 are attached on the side of the continuous base web 23 that will be a garment-facing side in the absorbent garment and the continuous base web 23 is then folded over on the garment-facing side of the continuous base web 23 and bonded in the folded-over configuration to the continuous base web 23 or to the elastic webs 24,25. In this manner the side of the continuous base web 23 that will be a body-facing side in the absorbent garment, will be smooth and without discontinuities. However, according to other embodiments of the invention, the waist elastic elements may be placed on the bodyfacing side of the continuous base web 23 and may be covered by a portion of the continuous base web 23 that is folded over towards the bodyfacing side of the continuous base web 23 to produce a continuous, seamless surface that will be facing a user's outer garments.

In the process in FIG. 1, the continuous base web 23 has a width that is equal to the width of the production web 22. This is a preferred arrangement since the continuous base web 23 will then be a carrier web for all components in the production web 22. Moreover, the continuous base web 23 will form a soft, comfortable and seam-free inner surface of an absorbent garment produced from the production web. The absence of seams on the inner surface is beneficial in that it reduces the risk of skin irritation. Moreover, by minimising the number of seams and joins in the absorbent garment, the garment becomes more flexible and conformable than prior art garments. The continuous base web 23 will also be a reinforcing member, reducing the risk of breaking seams and joins between other components in the garment and of tearing materials that have low tensile strength such as stretch-activated elastic laminates.

The elastic webs 24,25 in FIG. 1 are laminated to the continuous base web 23 in the lateral zones 3,4 but cover only a small portion of the edge zones 6,7. This means that the waist bands in the FIG. 1 embodiment will be formed mainly from the folded portions of the continuous base web 23 and the elastic elements 30,31 inside the folds. Waist elastic may alternatively be formed by applying the elastic webs 24,25 all the way to one or both edges 8,9 of the continuous base web 23 and folding the edge portions of the production web 22 to form a waist band comprising two layers of the elastic web 24,25. The waist band may optionally be supplemented with additional elastic elements. A further option is to create a waist band at one or both edges of the production web 22 by attaching elastic elements to the web and optionally covering the elastic elements with a separate nonwoven strip. The elastic elements 30,31 in FIG. 1 are shown as continuous threads. However, the elastic elements may be any type of elastic material that is used for elasticizing absorbent garments such as elastic bands and tapes comprising elastic nonwoven, laminates, film, net, foam, etc. The waist elastic does not have to be continuous as in FIG. 1 but can be in the form of discrete pieces of material attached intermittently along one or both edges of the production web 22.

Leg elastic 53 is applied to the production web 22 in a sinus curve pattern. The leg elastic can be any conventionally used elastic element such as one or more elastic threads, bands, etc. It is, of course possible to use further elastic elements to create leg elastic 53 and to apply the elastic elements in other patterns than the one shown herein. When the leg elastic is applied in a pattern extending across the cores, it may be advantageous to deactivate parts of the elastic element or elements extending over the cores 33. Deactivation may be accomplished in any known manner such as by treating the elastic members with chemicals or heat or by simply cutting the elastic members.

The leg elastic 53 may alternatively be applied to the production web 22 after the core components 32 have been added to the production web 22. A further option is to apply the leg elastic 53 to a carrier web that is then introduced in the process. One suitable way of arranging leg elastic on a production web is disclosed in WO 2004/078083.

When the production web 22 has been assembled, a portion 44 is cut out from the production web 22 between the core components 32 to create leg openings 45. The cut-out portions extend in the CD over the intermediate zone and into each lateral zone. In this manner, the elastic webs 24, 25 extend all the way to the leg openings in the finished garment 21. The production web and the integrated core components 32 are then folded centrally in the machine direction MD and the web halves are joined in side seams 46 between the core components. Finally, individual pant diapers 21 are cut from the production web.

Side joins are often arranged in a pant-type garment to connect the garment's front portion to the rear portion and to form a pant having a waist opening and leg openings. Usually, the side joins are intended to be arranged at the user's hips during use of the absorbent pants, but it is also known to arrange side joins more to the front of the garment. Side joins that are placed at the front of the garment may be made after severing individual garments from the production web. The side joins are preferably designed so that they can withstand the tensile forces which arise when the garment is being put on and is being worn, but such that they can be torn apart or opened in a controlled manner when the absorbent pants are taken off or to check if the garment needs changing. In the latter instance, the side joins are preferably reclosable joins, as known in the art.

Moreover, if the garment is an open-type diaper of the kind that is fastened together into a pant-shape when the diaper is put on a user, the process does not involve forming side seams. Instead, the process will normally include arranging fastening elements on the production web or on the garments after they have been cut from the web. Commonly used fastening elements for open-type diapers are mating hook-and-loop fasteners or adhesive fasteners.

Figure 3:
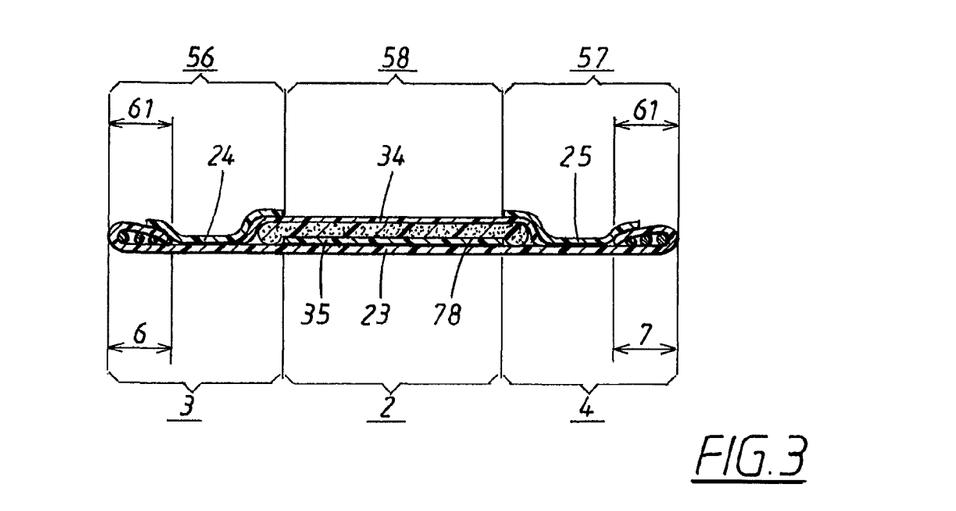
FIG. 3 shows a cross section through a production web according to the invention.

FIG. 3 is a section through the production web 22 taken in the cross machine direction, CD, before folding of the web and cutting it into individual absorbent garments. Accordingly, FIG. 3 shows a longitudinal section through an absorbent garment that may be a pant diaper or sanitary panty that has not yet been folded and provided with side seams or the absorbent garment may be an open-type diaper.

When seen as components in an absorbent garment, the continuous base web 23 forms a liquid permeable topsheet 78 on the inside or body-facing side of the absorbent garment. The continuous base web also extends into and forms part of front and back elastic waist bands 61 or waist panels. The elastic webs 24,25 that are laminated to the continuous base web 23 form front and back panels 56,57 of a chassis structure that also includes a crotch panel 58 including the liquid barrier layer 34 of the core component 32. FIG. 3 does not show all the different elements and layers of the core component. However, a liquid acquisition layer 35 is shown between the absorbent core 33 and the liquid permeable topsheet 78. The liquid handling layer is somewhat shorter than the absorbent core 33. Similarly, it is usually desirable that the liquid handling layer has a smaller width than the absorption core 33. The liquid barrier layer 34 may be covered by an outer crotch nonwoven that is not shown in the figures. The outer crotch nonwoven should preferably be chosen to be a non-elastic material to ensure that the crotch portion of the garment according to the invention is generally non-elastic.

The elastic webs 24,25 are shown in FIGS. 1 and 2 to extend in over the absorbent core 33 of the core component 32. However, in an alternative embodiment, the elastic webs 24,25 may be applied to the continuous base web 23 without overlap with the absorbent core 33. Preferably, the elastic webs 24,25 extend all the way to the leg opening cut-outs 45 so that the front and back panels of the finished absorbent garment 21 extend all the way to the leg openings. Similarly, the elastic webs 24,25 may extend all the way to into the elastic waist bands 61 and even be folded together with the continuous base web 23 in the waist bands 61. However, there is preferably a gap between the elastic webs 24,25 in the crotch panel 58. This means that the edges of the elastic webs 24,25 that are farthest away from the edges 8,9 of the production web are located at distance from each other. The crotch panel 58 is located in a part of the absorbent article that will normally be generally non-elastic due to the absorbent core being non-elastic.

The process according to the invention may in a conventional manner include the application of further elements such as elasticised or non-elasticised barriers, lotion, odour control agents, shaping elements, stabilising elements, etc.

Particularly, the process may include treating the continuous base web 23 so that it is provided with areas of different hydrophilicity or hydrophobicity. Hydrophobic polymeric materials are commonly used in topsheets for absorbent articles. In order to improve liquid permeability, the materials are treated with surfactants or by modification of the surface of the materials to render them more hydrophilic. Preferably, a portion of the continuous base web that covers the absorbent cores is treated to render it more hydrophilic or less hydrophobic than portions of the base web 23 that are located outside of the absorbent cores. Accordingly, the more hydrophobic portions of the base web may be used to form the elastic waist band and those parts of the back and front panels that are not coincident with the cores. A simple way of accomplishing differential hydrophilicity in the continuous base web 23 is to treat an area of the base web 23 extending in the MD and having a width that is equal to the length of the absorbent cores. Alternatively, the treatment may be carried out intermittently, so that the parts of the continuous base web 23 located between the absorbent cores in the MD are left untreated.

It is alternatively possible to use a hydrophilic base web 23 and treat the portions that should be less hydrophilic or more hydrophobic with a hydrophobicity enhancing agent.

Figure 4:
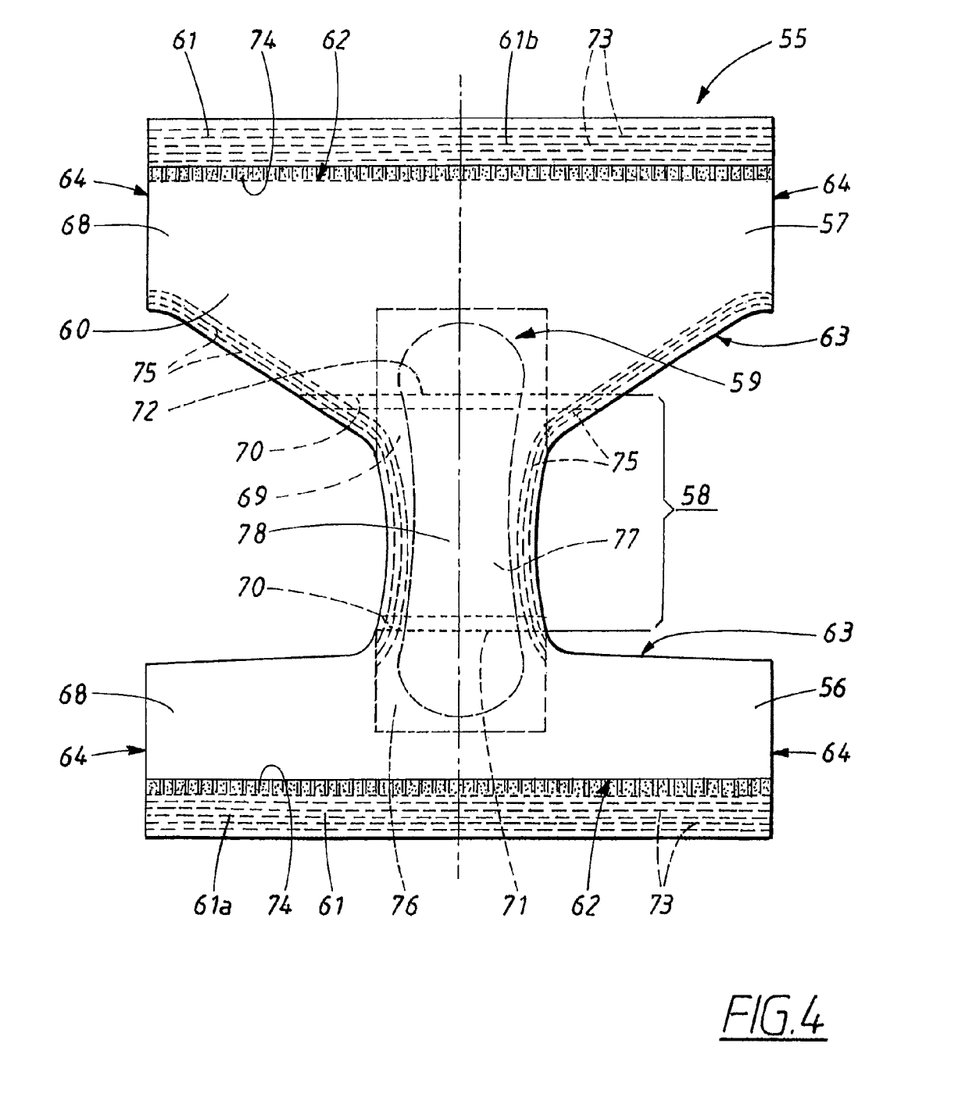
FIG. 4 shows a pant-type diaper in accordance with the invention in a flat state.
Figure 5:
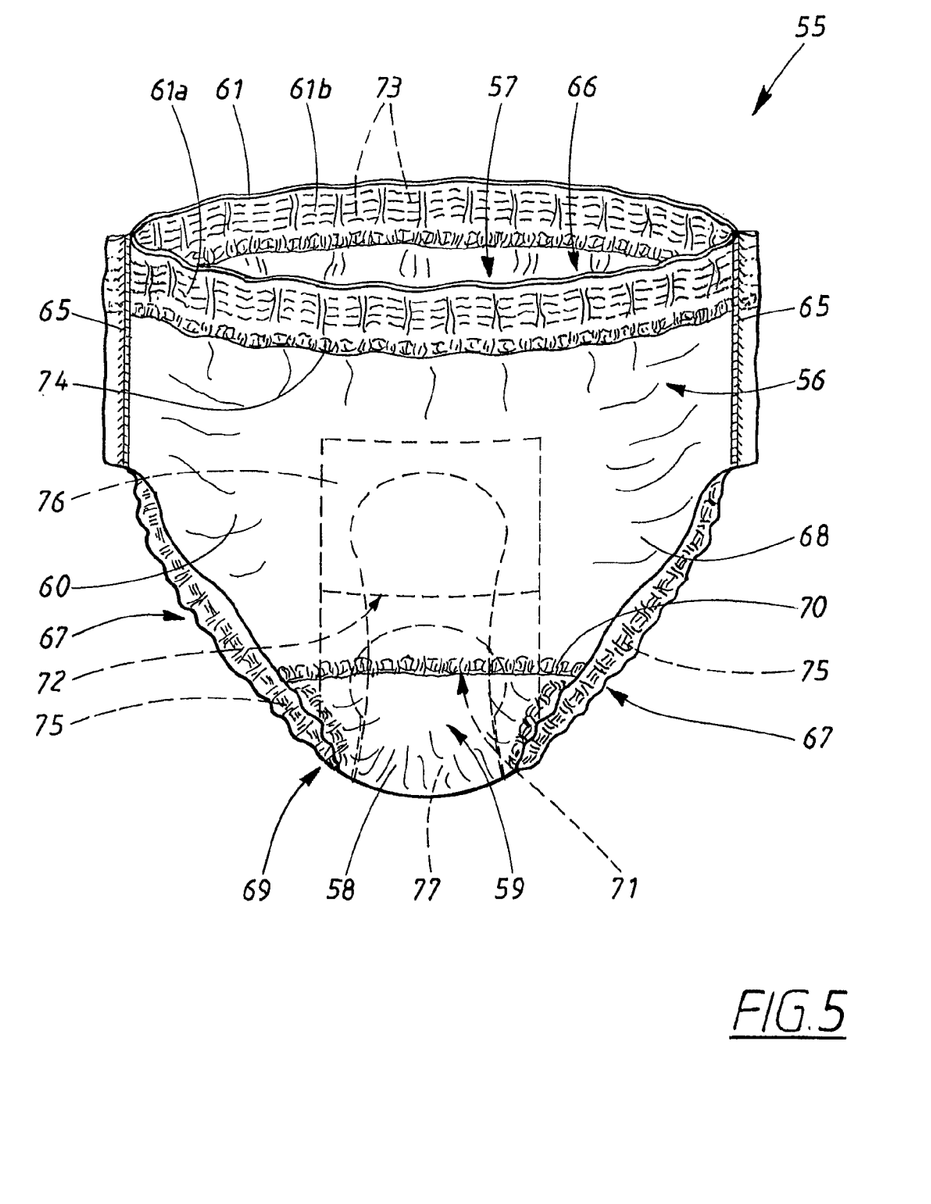
FIG. 5 shows the diaper in FIG. 4 with closed side joins.

The pant diaper 55 shown in FIGS. 4 and 5 is designed to enclose the lower part of a wearer's trunk in the manner of conventional underwear. In FIG. 4, the diaper 55 is shown from the inside, i.e. from the side facing the wearer when the garment is worn and in FIG. 5, the diaper is shown from the outside, or the garment-facing side, which is the side that is facing away from the wearer when the diaper is worn. In FIG. 4 the diaper is shown in a flat state with all elastic elements in a stretched-out state and in FIG. 5 the diaper is shown as it appears when it is worn, with partially contracted elastic elements and with closed side seams.

The diaper has a front panel 56, a back panel 57 and a crotch panel 58 extending between the front and back panels 56,57 and having a relatively narrow width as compared to the front and back panels 56,57. The front and back panels 56,57 are arranged to cover the wearer's hips and to extend over the belly and the back of the wearer to encircle the lower part of the wearer's trunk.

The diaper 55 further comprises a core region 59 extending from the crotch panel 58 into the front panel 56 and the back panel 57. The front and back panels 56,57 form part of a diaper chassis. The chassis 60 comprises the front panel 56, the back panel 57 the crotch panel 58 and an elastic waist band 61 arranged at the front and back panels 56,57. Each of the front and back panels 56,57 has a waist edge 62 a crotch edge 63 and a pair of side edges 64.

The term "panel" is used herein to denote a delimited part of the diaper chassis having defined boundaries while the terms "region" and "portion" are used to denote the approximate location of a particular feature of the diaper in the chassis or to describe the intended positioning of a particular part of the diaper in relation to a user's body. A panel may be formed from separate materials or may be completely or partially formed from materials that also extend into one or more contiguous panels. A region or portion may have an extension fully or partially covering one or more panels. The chassis is defined as the part of the pant-type absorbent garment supporting the absorbent component and comprises inner and outer covering layers, elastic elements, etc.

When components are joined, attached or secured to each other, they are originally separate parts that have been bonded by any suitable means such as adhesively, by stitching or by ultrasonic welding or thermo-welding. The term joined is also intended to include separable (openable) joins, such as separable side joins and reclosable joins such as hook-and loop joins, reclosable tape joins, snap fasteners, etc. Components that have been arranged on each other need not be bonded, although as used herein, the term "arranged" is intended to also include bonded configurations.

The front and back panels 56,57 have been joined to each other along their side edges 64 by thermobonding, ultrasonic welding, glue strings or the like to form side seams 65, as shown in FIG. 5. The elastic waist band 61 consists of a front waist panel 61a and a back waist panel 61b, extending from the front panel 56 and the back panel 57, respectively. The front and back waist panels 61a, 61b are also joined to each other along the side seams 65. By joining the front and back panels 56, 57 and the waist panels 61a, 61b, along the side seams 65, the pant diaper 55 is provided with a waist opening 66 and a pair of leg openings 67.

FIG. 4 shows the diaper 55 in a flat state with any elastic components that are attached to the chassis 60 under tensional stress drawn out to the fully extended dimensions of the chassis 60. FIG. 5 shows the pant diaper 55 as it appears when the side seams 65 have been formed and the tensioned elastic elements have been allowed to relax and gather the chassis material to form elasticized leg openings 67 and an elasticized waist opening 66.

In accordance with the invention, the front and back panels 56,57 include an elastic material 68 that has been laminated to a non-elastic nonwoven layer arranged on the inside of the diaper. The front and back panels 56,57 are preferably elastically stretchable at least in the direction of the waist edges 62 but may also be elastically stretchable perpendicular to the waist edges 62, in the direction of the side edges 64. The elastic material 68 and the front and back panels 56,57 extend from the waist edges 62 all the way to the leg openings 67.

The crotch panel 58 is the part of the chassis that is located between the front and back panels 56, 57 in the longitudinal direction of the diaper 55. The crotch panel is formed from a nonwoven crotch material 69 that has been joined to the front and back panels 56,57 at crotch seams 70. Hence, the crotch material 69 which is a non-elastic material, such as a non-elastic nonwoven material overlaps slightly with the elastic front and back panels 56,57. The crotch material 69 is joined along its transverse edges 71,72 to the front and back panels 56,57 at the overlapping portions. The joining can be made in any suitable way such as by ultrasonic welding, adhesively or similar.

The planar extension of the core region 59 is defined by a liquid-impervious barrier sheet 76 arranged between an absorbent core 77 and the chassis 60. The liquid-impervious barrier sheet 76 is shown to have a rectangular shape and the absorbent core 77 is hour-glass shaped. However, both the barrier sheet 76 and the absorbent core 77 may have alternative shapes.

As an alternative to the embodiment shown in FIGS. 4 and 5, it is possible to dispense with the nonwoven crotch material. In such an embodiment, the liquid-impervious barrier sheet 76 forms the crotch panel of the chassis.

A liquid permeable topsheet 78 is arranged over the core 77 and the liquid-impervious barrier sheet 76. The topsheet 78 forms a continuous inner surface of the diaper chassis 60 and consists of a layer of nonwoven material or a liquid permeable laminate comprising a nonwoven layer.

The liquid-impervious barrier sheet 76 can consist of a liquid-impermeable plastic film, a nonwoven sheet which has been coated with a liquid barrier material, or some other flexible material sheet which has the ability to withstand liquid penetration. However, it can be advantageous if the liquid-impervious barrier sheet 76 is breathable, i.e. permits the passage of water vapour through the sheet 76.

The absorption core 77 comprises absorbent material, such as cellulose fluff pulp, tissue, absorbent foam, etc. It is also possible for the absorption core to contain superabsorbents, i.e. polymer materials which are able to absorb body fluid corresponding to many times their own weight and form a hydrogel. Superabsorbents are usually provided in the form of particles, but fibres, flakes, granules and films are also available. Moreover, the absorption core 77 can comprise non-absorbent components such as stiffening elements, shaping elements, binders, etc. Various types of liquid-receiving porous structures such as fibre wads, open-cell foam or the like can also be included in the core.

The absorption core 77 may be produced separately and included in a "core pack" that is subsequently integrated in the diaper chassis as shown in FIGS. 1 and 2. The various components included in the core pack can be connected to one another in a conventional manner, for example by adhesive bonding, ultrasonic welding or thermowelding. The core pack comprises at least an absorbent core having a barrier layer applied as a carrier layer on one surface of the core. Preferably, a liquid permeable layer such as a liquid acquisition layer is applied to the opposite side of the core. Further components such as elastic members, shape-stabilizing members, shaping elements or the like may also be included.

In the diaper shown in FIGS. 4 and 5, the elastic waist band 61 is formed from extensions of the continuous inner nonwoven topsheet material at the waist edges 62. The nonwoven material has been elasticized by one or more elongate elastic members 73, such as elastic threads or bands. The elastic members 73 have been attached to an edge portion of the nonwoven topsheet 78 material whereafter the topsheet material has been folded to cover the elastic members 73 and has been secured in the folded configuration in a waist band join 74. The elastic members 73 may be secured on the side of the nonwoven topsheet material 78 that forms the inner surface of the diaper 55 or on the opposite side. Preferably, the elastic members 73 are arranged on the surface that is opposite to the inner surface of the diaper so that the folded-over portion of the nonwoven material if folded towards the outside of the diaper 55 leaving a smooth, continuous surface without any seams or edges on the inside of the diaper. It is alternatively possible to attach elastic elements to an edge portion of the topsheet material 78 and leave the elastic elements non-covered, or covered by a separate web. Further, the elastic waist band 61 may incorporate portions of the elastic webs arranged at the front and back panels 55,66. The elastic webs may be folded to create an edge portion having higher elastic retraction force than a single-layer elastic web. The folded elastic web may be supplemented by additional elastic elements, if desired.

The elastic members 73 are arranged in the waist band 61 in a tensioned state such that they contract and gather the nonwoven material in the waist band 61 when they are allowed to relax, as shown in FIG. 5.

In an alternative, less preferred embodiment, the elastic waist band 61 can be a component that is prefabricated and joined to the outside or the inside of the front and back panels 56,57 respectively. The waist band join 74 between the waist band 61 and the front and back panels 56,57 can be made in any suitable way such as by means of ultrasonic welding, heat welding, or adhesively.

Elastic members 75 are also arranged along the edges of the leg openings 67 and form leg elastic. The elastic members 75 at the leg openings can be any kind of conventional elastic elements such as elastic threads, bands, foam strips, or similar.

The core region 59 extends into the front and back panels 56,57 so that the elastic web 68 in these panels overlap with the liquid-impervious barrier sheet 76 in the outer parts of the core region 59 as seen in FIG. 4. The elastic web 68 is arranged on the garment-facing side of the liquid-impervious barrier sheet 76.

The continuous inner nonwoven topsheet material has preferably been treated so that the portions of the material covering the absorbent core are more hydrophilic than portions of the topsheet material being located outside the intended fluid-receiving area of the article.

The elastic web 68 in the front and back panels 56,57 preferably comprises a nonwoven web that is arranged on the outside of the diaper to create a textile outer garment-facing surface of the diaper. Alternatively, the elastic web may consist of or include an elastic film that forms an outer surface of the diaper.

Elasticity Test

The method measures how an elastic material behaves at cycles of repeated load and unload. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample I centred and fastened perpendicularly in the clamps. The tensile tester is started and three cycles between 0 and the predetermined elongation equal to the highest defined $1^{st}$ load are performed. Before the last cycle, the sample is relaxed for 1 minute, then the permanent elongation is measured by stretching the sample until a force of 0.1 N is detected and the elongation is read.

An elastic material is defined as a material having a permanent elongation after relaxation of less than 10% after the material has been subjected to an elongation of 30% in the test above. An elongation of 30% means an elongation to a length that is 30% longer than the initial length of the sample.

A non-elastic material has a permanent elongation after relaxation of more than 10% after having been subjected to an elongation of 30%.

The invention claimed is:

1. A method for continuously producing absorbent garments comprising (i) forming a continuous multi-component production web and (ii) cutting individual garments from the production web, wherein
   (i) comprises:
   a) feeding a continuous web of liquid permeable material in a travelling direction, the web of liquid permeable material having lateral edges parallel to the travelling direction, and the web of liquid permeable material having an intermediate zone extending in the travelling direction and a first lateral zone and a second lateral zone on each side of the intermediate zone;
   b) intermittently laying down absorbent cores in the intermediate zone of the continuous web of liquid permeable material;
   c) feeding a first elastic web in the travelling direction;
   d) stretching the first elastic web by 35-250% in the travelling direction; and
   e) bonding the first elastic web to the continuous web of liquid permeable material within the boundary defined by the first lateral zone of the continuous web of liquid permeable material so that the the first elastic web does not extend beyond the lateral edges of the web of liquid permeable material.

2. The method according to claim 1, wherein (i) further comprises:
   f) feeding a second elastic web in the travelling direction;
   g) stretching the second elastic web by 35-250% in the travelling direction; and
   h) bonding the second elastic web to the continuous web of liquid permeable material in the second lateral zone of the continuous web of liquid permeable material.

3. The method according to claim 2, wherein the first and second elastic webs are bonded to the continuous web of liquid permeable material with a gap between the first and second elastic webs in the intermediate zone.

4. The method according to claim 2, wherein at least one of the first and second elastic webs comprises an elastic film.

5. The method according to claim 2, wherein at least one of the first and second elastic webs comprises an elastic nonwoven material.

6. The method according to claim 2, wherein at least one of the first and second elastic webs is a laminate of an elastic film and a nonwoven layer and is bonded to the continuous web of liquid permeable material with the elastic film facing the continuous web of liquid permeable material.

7. The method according to claim 2, wherein at least one of the first and second elastic webs comprises a stretch-activated elastic laminate.

8. The method according to claim 2, wherein at least one of the first and second elastic webs comprises a stretch-bonded elastic laminate.

9. The method according to claim 2, wherein at least one of the first and second elastic webs is adhesively bonded to the continuous web of liquid permeable material.

10. The method according to claim 2, wherein at least one of the first and second elastic webs is thermally or ultrasonically bonded to the continuous web of liquid permeable material.

11. The method according to claim 1, wherein the continuous web of liquid permeable material is a nonwoven web.

12. The method according to claim 1, wherein the cores are at least partially covered with a liquid impermeable material on a surface of the cores facing away from the continuous web of liquid permeable material.

13. The method according to claim 1, wherein a leg elastic member is attached to the production web.

14. The method according to claim 1, wherein the production web is provided with an elastic waist band along at least one edge of the production web and extending in a direction parallel to the travelling direction.

15. The method according to claim 14, wherein the elastic waist band comprises a portion of the continuous web of liquid permeable material.

16. The method according to claim 14, wherein the elastic waist band is joined to the production web as a separate component.

17. The method according to claim 1, wherein (i) further comprises treating the continuous web of liquid permeable material to provide a continuous web of liquid permeable material with areas of different hydrophilicity or hydrophobicity.

18. The method according to claim 17, wherein the continuous web of liquid permeable material comprises a hydrophobic polymeric material and the continuous web of liquid permeable material is subjected to a hydrophilicity treatment in a selected portion or portions of the continuous web of liquid permeable material coinciding with the absorbent cores in the production web.

19. The method according to claim 1, wherein (i) further comprises one or more of the following production steps:
   a) applying leg elastic;
   b) applying raised barriers;
   c) cutting the production web to form leg openings;
   d) folding the production web;
   e) applying fastening elements to the production web;
   f) forming side joins in the folded web, and
   g) separating individual pant-type absorbent garments from the production web by cutting at the side joins.

20. The method according to claim 1, wherein the first elastic web is first cut during step (ii).

21. A method for continuously producing absorbent garments comprising (i) forming a continuous multi-component production web and (ii) cutting individual garments from the production web, wherein
   (i) comprises:
   a) feeding a continuous web of liquid permeable material in a travelling direction, the web of liquid permeable material having an intermediate zone extending in the travelling direction and a first lateral zone and a second lateral zone on each side of the intermediate zone;
   b) intermittently laying down absorbent cores in the intermediate zone of the continuous web of liquid permeable material;
   c) feeding a first elastic web in the travelling direction;
   d) stretching the first elastic web by 35-250% in the travelling direction; and e) bonding the first elastic web to the continuous web of liquid permeable material in the first lateral zone of the continuous web of liquid permeable material wherein the cores are at least partially covered with a liquid impermeable material on a surface of the cores facing away from the continuous web of liquid permeable material, and wherein the cores are applied and bonded to the liquid impermeable material before joining the cores with the continuous web of liquid permeable material.

22. The method according to claim 21, wherein the cores are turned and/or rotated after being bonded to the liquid impermeable material and are brought into a facing relationship with the continuous web of liquid permeable material and are applied to the continuous web of liquid permeable material with the longitudinal direction of the cores aligned with a cross-machine direction of the continuous web of liquid permeable material.

23. An absorbent garment comprising a longitudinal direction and a transverse direction, a chassis structure comprising a longitudinal centerline, a front panel having a front transverse end edge along the transverse direction and first and second side edges, a back panel having a back transverse end edge along the transverse direction and first and second side edges, a crotch panel being arranged between the front and back panels, and elasticated front and back waist panels being arranged along the front and back transverse end edges of the front and back panels and extending across the longitudinal centerline, and a core component being integrated with the chassis structure and forming an integral part of the absorbent garment, the chassis structure including a liquid permeable material having a garment facing side and a user facing side and forming a liquid permeable surface layer in the garment, wherein the liquid permeable material extends continuously between the front end edge and the back end edge and at least one of the front panel and the back panel comprises an elastic web that has been bonded to the liquid permeable material with the elastic web stretched by 35-250% in at least one direction, and that extends across the longitudinal centerline.

24. The absorbent garment according to claim 23, wherein the liquid permeable material forms part of one or both of the elasticated front and back waist panels.

25. The absorbent garment according to claim 23, wherein an elastic web has been bonded to each of the front panel and the back panel, the garment having a gap between the elastic webs in the crotch panel.

26. The absorbent garment according to claim 23, wherein the first and second side edges of the front panel are joined by edge joins to the corresponding first and second side edges of the back panel.

27. The absorbent garment according to claim 23, wherein the elastic waist panels comprise elastic elements that are attached to the liquid-permeable material.

28. The absorbent garment according to claim 27, wherein the elastic elements are attached to the outer garment-facing side of the liquid-permeable material.

29. The absorbent garment according to claim 27, wherein the elastic elements are attached to the user-facing side of the liquid-permeable material.

30. The absorbent garment according to claim 27, wherein the liquid-permeable material is folded over to cover the elastic elements and is secured in the folded over configuration.

31. The absorbent garment according claim 23, wherein the elastic waist panels comprise a portion of the at least one elastic web.

32. The absorbent garment according to claim 23, wherein the liquid permeable material is treated to render it more hydrophilic or less hydrophobic in an area of the liquid permeable material that covers the absorbent core than in an area of the liquid permeable material that is located outside of the absorbent core.

* * * * *